US010973581B2

(12) United States Patent
Mariampillai et al.

(10) Patent No.: US 10,973,581 B2
(45) Date of Patent: Apr. 13, 2021

(54) SYSTEMS AND METHODS FOR OBTAINING A STRUCTURED LIGHT RECONSTRUCTION OF A 3D SURFACE

(71) Applicant: 7D SURGICAL INC., Toronto (CA)

(72) Inventors: Adrian Mariampillai, Toronto (CA); Kenneth Kuei-Ching Lee, Toronto (CA); Michael Leung, Markham (CA); Peter Siegler, Toronto (CA); Beau Anthony Standish, Toronto (CA); Victor X. D. Yang, North York (CA)

(73) Assignee: 7D SURGICAL INC., Toronto (CA)

( * ) Notice: Subject to any disclaimer, the term of this patent is extended or adjusted under 35 U.S.C. 154(b) by 83 days.

(21) Appl. No.: 16/304,528

(22) PCT Filed: Jun. 16, 2017

(86) PCT No.: PCT/CA2017/050743
§ 371 (c)(1),
(2) Date: Nov. 26, 2018

(87) PCT Pub. No.: WO2017/214735
PCT Pub. Date: Dec. 21, 2017

(65) Prior Publication Data
US 2019/0133692 A1 May 9, 2019

Related U.S. Application Data

(60) Provisional application No. 62/351,622, filed on Jun. 17, 2016.

(51) Int. Cl.
*G06K 9/00* (2006.01)
*A61B 34/10* (2016.01)
(Continued)

(52) U.S. Cl.
CPC .............. *A61B 34/10* (2016.02); *A61B 90/30* (2016.02); *A61B 90/37* (2016.02); *G01B 11/245* (2013.01);
(Continued)

(58) Field of Classification Search
CPC ....... G01B 11/245; G01B 11/25; A61B 90/30; A61B 90/37; A61B 2034/2055; A61B 2090/373; A61B 34/10
See application file for complete search history.

(56) References Cited

U.S. PATENT DOCUMENTS 7,385,708 B2    6/2008   Ackerman et al.
9,119,670 B2    9/2015   Yang et al.
(Continued)

OTHER PUBLICATIONS

International Search Report for the parent PCT/CA2017/050743 application, dated Sep. 26, 2017.

*Primary Examiner* — Amara Abdi
(74) *Attorney, Agent, or Firm* — Hill & Schumacher

(57) ABSTRACT

Disclosed are systems and methods for obtaining a structured light reconstruction using a hybrid spatio-temporal pattern sequence projected on a surface. The method includes projecting a structured light pattern, such as a binary de Bruijn sequence, onto a 3D surface and acquiring an image set of at least a portion of this projected sequence with a camera system, and projecting a binary edge detection pattern onto the portion of the surface and acquiring an image set of the same portion of the projected binary pattern. The acquired image set of the binary pattern is processed to determine edge locations therein, and then employed to identify the locations of pattern edges within the acquired image set of the structured light pattern. The detected edges of the structured light pattern images are employed to decode the structured light pattern and calculate a disparity map, which is used to reconstruct the 3D surface.

56 Claims, 12 Drawing Sheets

(51) Int. Cl.
*G01B 11/245* (2006.01)
*G01B 11/25* (2006.01)
*A61B 90/30* (2016.01)
*A61B 90/00* (2016.01)
*A61B 34/20* (2016.01)

(52) U.S. Cl.
CPC ...... *G01B 11/25* (2013.01); *A61B 2034/2055* (2016.02); *A61B 2090/373* (2016.02)

(56) References Cited

U.S. PATENT DOCUMENTS

| | | | |
|---|---|---|---|
| 9,325,973 | B1 | 4/2016 | Hazeghi et al. |
| 10,247,672 | B2* | 4/2019 | Betzig ................ G01N 21/6428 |
| 2014/0002605 | A1 | 1/2014 | Liao et al. |
| 2014/0037146 | A1* | 2/2014 | Taguchi .................. G06T 7/521 |
| | | | 382/107 |
| 2014/0078264 | A1* | 3/2014 | Zhang ..................... G06T 7/521 |
| | | | 348/47 |
| 2015/0204663 | A1* | 7/2015 | Znamenskiy ........... G06T 7/586 |
| | | | 348/46 |
| 2015/0300816 | A1* | 10/2015 | Yang .................. G01N 21/4738 |
| | | | 600/424 |
| 2016/0182889 | A1* | 6/2016 | Olmstead ........... G01B 11/2513 |
| | | | 348/47 |

* cited by examiner

| Subpixel Interpolation Method | Order of de Bruijn Sequence | Number of Patterns Required |
|---|---|---|
| Zero Crossing | $\log_2 C - n_g$ | $n_g + \log_2 C + 1$ |
| Intersection | $\log_2 C - n_g$ | $2n_g + \log_2 C + 2$ |
| Comb Intersection Subdivision Zero Crossing | $\log_2 C - n_g$ | $n_g + \log_2 C + 2$ |
| Comb Zero Crossing Subdivision Intersection | $\log_2 C - n_g$ | $2n_g + \log_2 C + 1$ |

SYSTEMS AND METHODS FOR OBTAINING A STRUCTURED LIGHT RECONSTRUCTION OF A 3D SURFACE

CROSS-REFERENCE TO RELATED APPLICATION

This application is a National Phase application claiming the benefit of the international PCT Patent Application No. PCT/CA2017/050743, filed on Jun. 16, 2017, in English, which claims priority to U.S. Provisional Application No. 62/351,622, titled "SYSTEM AND METHOD FOR OBTAINING A STRUCTURED LIGHT RECONSTRUCTION OF A 3-D SURFACE" and filed on Jun. 17, 2016, the entire contents of which are incorporated herein by reference.

BACKGROUND

The present disclosure relates to surface detection and imaging using structured light.

Real-time, robust, accurate structured light can enable novel applications for imaging patient anatomy within an operating room environment. Structured light systems work by projecting one or more patterns onto a scene, and recording those patterns with one or more cameras to create a depth map (or disparity map) that approximates the scene (i.e., a 3D surface) on which the pattern is projected. A 3D point cloud of the scene can be reconstructed from the depth map by triangulation.

To use triangulation, the optical system must be calibrated, so that the relative position and orientation and intrinsic optical properties of the optical components are known. There are two widely reported and utilized structured light system types. These systems types are 1) a system comprising two or more calibrated stereo cameras used with an uncalibrated projector, and 2) a system comprising a calibrated single camera with a calibrated projector. For system 1, a minimum of two calibrated cameras is used to capture the images of the projected pattern. From these captured images the disparity between the two views can be calculated. In system 2), the image of the projected pattern from one or more cameras is directly compared against a stereo rectified and undistorted projected pattern.

Many different techniques for performing structured light detection and imaging have been reported, (see for example J. Salvi, J. Pagès, and J. Batlle. "Pattern codification strategies in structured light systems; Pattern Recognition", 37(4):827-849, 2004, herein after [Salve 2004], which is incorporated herein by reference in its entirety), such as methods based on temporal-multiplexing, spatial neighborhoods, and direct coding. In temporal-multiplexing based methods, multiple patterns are projected onto the scene as a function of time to encode regions of the scene for robust stereo-matching. The encoding robustness typically increases with the number of patterns used at the expense of increasing acquisition time, making time-based methods more suitable for reconstructing static scenes with high accuracy and point density.

In comparison, spatial methods can use as few as one unique pattern similar to a barcode or QR code to encode the scene, making these methods more suitable for reconstructing dynamic scenes due to the short image acquisition time. However, spatial neighborhood based methods require the entire local neighborhood of a point to be reconstructed to be visible in the acquired image(s) in order to accurately reconstruct the point. This constraint, known as the local smoothness approximation, is prone to breaking down in regions of the 3D target with sharp changes in elevation (the direction going away from the structured light system) (i.e. large slopes). Violation of the local smoothness approximation leads to data loss and/or corruption in these regions of the reconstruction.

SUMMARY

Disclosed are systems and methods for obtaining a structured light reconstruction using a hybrid spatio-temporal pattern sequence projected on a surface. The method includes projecting a structured light pattern, such as a binary de Bruijn sequence, onto a 3D surface and acquiring an image set of at least a portion of this projected sequence with a camera system, and projecting a binary edge detection pattern onto the portion of the surface and acquiring an image set of the same portion of the projected binary pattern. The acquired image set of the binary pattern is processed to determine edge locations therein, and then employed to identify the locations of pattern edges within the acquired image set of the structured light pattern. The detected edges of the structured light pattern images are employed to decode the structured light pattern and calculate a disparity map, which is used to reconstruct the 3D surface.

Accordingly, in one example embodiment, there is provided a method for obtaining structured light reconstruction of a 3D surface using a structured light system comprising a projector, and a first camera and a second camera, the method comprising:

employing the projector to project a structured light pattern onto the 3D surface;

acquiring, with the first camera and the second camera, respective structured light images of the projected structured light pattern;

employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein transition edges correspond to boundaries between adjacent elements having different states, and wherein non-transition edges correspond to boundaries between adjacent elements having a common state;

acquiring, with the first camera and the second camera, respective binary edge detection images of the projected binary edge detection pattern;

processing each binary edge detection image to identify, within each binary edge detection image, locations of the transition edges;

determining edge locations of elements within the structured light images, wherein the locations of the transition edges of the binary edge detection images are employed to identify corresponding non-transition edges within the respective structured light images;

employing the edge locations within the structured light images to decode the structured light pattern within the structured light images;

performing stereo matching of the decoded structured light images and obtaining a disparity map; and generating a reconstruction of the 3D surface based on the disparity map.

In another example embodiment, there is provided a method for obtaining structured light reconstruction of a 3D surface using a structured light system comprising a projector and a camera, the method comprising:

employing the projector to project a structured light pattern onto the 3D surface;

acquiring a structured light image of the projected structured light pattern with the camera;

employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein the transition edges correspond to boundaries between adjacent elements having different states, and the non-transition edges correspond to boundaries between adjacent elements having a common state;

acquiring a binary edge detection image of the projected binary edge detection pattern with the camera;

processing the binary edge detection image to identify locations of the transition edges;

determining edge locations of elements within the structured light image, wherein the locations of the transition edges of the binary edge detection image are employed to identify corresponding non-transition edges within the structured light image;

employing the edge locations within the structured light image to decode the structured light pattern within the structured light image;

performing stereo matching of the decoded structured light image with a reference and obtaining a disparity map; and generating a reconstruction of the 3D surface based on the disparity map.

In another example embodiment, there is provided a system for obtaining structured light reconstruction of a 3D surface, the system comprising:

a projector configured to project patterns onto a surface;

a first camera and a second camera, wherein the first camera and the second camera are oriented to image the patterns projected by the projector; and computer hardware operatively coupled to said projector, said first camera and said second camera, wherein said computer hardware comprises memory coupled with one or more processors to store instructions, which when executed by the one or more processors, causes the one or more processors to perform operations comprising:

employing the projector to project a structured light pattern onto the 3D surface;

acquiring, with the first camera and the second camera, respective structured light images of the projected structured light pattern;

employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein transition edges correspond to boundaries between adjacent elements having different states, and wherein non-transition edges correspond to boundaries between adjacent elements having a common state;

acquiring, with the first camera and the second camera, respective binary edge detection images of the projected binary edge detection pattern;

processing each binary edge detection image to identify, within each binary edge detection image, locations of the transition edges;

determining edge locations of elements within the structured light images, wherein the locations of the transition edges of the binary edge detection images are employed to identify corresponding non-transition edges within the respective structured light images;

employing the edge locations within the structured light images to decode the structured light pattern within the structured light images;

performing stereo matching of the decoded structured light images and obtaining a disparity map; and generating a reconstruction of the 3D surface based on the disparity map.

In another example embodiment, there is provided a system for obtaining structured light reconstruction of a 3D surface, the system comprising:

a projector configured to project patterns onto a surface;

a camera oriented to image the patterns projected by the projector; and computer hardware operatively coupled to said projector and said camera, wherein said computer hardware comprises memory coupled with one or more processors to store instructions, which when executed by the one or more processors, causes the one or more processors to perform operations comprising:

employing the projector to project a structured light pattern onto the 3D surface;

acquiring a structured light image of the projected structured light pattern with the camera;

employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein the transition edges correspond to boundaries between adjacent elements having different states, and the non-transition edges correspond to boundaries between adjacent elements having a common state;

acquiring a binary edge detection image of the projected binary edge detection pattern with the camera;

processing the binary edge detection image to identify locations of the transition edges;

determining edge locations of elements within the structured light image, wherein the locations of the transition edges of the binary edge detection image are employed to identify corresponding non-transition edges within the structured light image;

employing the edge locations within the structured light image to decode the structured light pattern within the structured light image;

performing stereo matching of the decoded structured light image with a reference and obtaining a disparity map; and generating a reconstruction of the 3D surface based on the disparity map.

In another example embodiment, there is disclosed a method for obtaining a structured light reconstruction of a 3D surface using a calibrated projector-camera(s) system utilizing one or more cameras, comprising:

a) projecting a pattern comprised of at least one binary de Bruijn sequence, onto at least a portion of the 3D surface;

b) acquiring an image set of at least a portion of said pattern of said projected binary de Bruijn sequence with said one or more cameras;

c) projecting at least one binary pattern onto said at least a portion of the 3D surface;

d) acquiring an image set of at least a portion of said projected binary pattern with said one or more cameras;

e) for each image within said image sets acquired in steps b) and d), decimating said acquired image set of said binary de Bruijn sequence using said acquired image set of said binary pattern and calculating a location of all pattern edges within said acquired image set of said binary de Bruijn sequence;

f) determining correspondences between the pattern edges calculated in step e) and the projected binary de Bruijn sequence and from said correspondences calculating a disparity map; and g) reconstructing the 3D surface using said disparity map.

In another example embodiment, there is disclosed a method for obtaining a structured light reconstruction of a 3D surface using a projector and calibrated stereo camera system, comprising:

a) projecting a pattern comprised of at least one binary de Bruijn sequence, onto at least a portion of the 3D surface;

b) acquiring an image set of at least a portion of said pattern of said projected binary de Bruijn sequence using two or more stereo calibrated cameras;

c) projecting at least one binary pattern onto said at least a portion of the 3D surface;

d) acquiring an image set of at least a portion of said projected binary pattern with said two or more stereo calibrated cameras;

e) for each image within said image sets acquired in steps b) and d), decimating said acquired image set of said binary de Bruijn sequence using said acquired image set of said binary patterns and calculating a location of all pattern edges within said acquired image set of said binary de Bruijn sequence;

f) determining correspondences between the pattern edges in the image sets and from said correspondences calculating a disparity map; and g) reconstructing the 3D surface using said disparity map.

In an embodiment the binary pattern may be a binary comb pattern that spans only contiguous regions of the de Bruijn sequence.

In another example embodiment the binary pattern is a binary comb pattern having alternating black and white comb elements of equal width.

In another example embodiment, the method may further include:

h) projecting at least one additional binary pattern onto said portion of said 3D surface;

i) acquiring an additional image set of at least a portion of said additional binary pattern with said one or more cameras; and wherein step e) includes decimating said acquired image set of said at least a portion of said pattern of said projected binary de Bruijn sequence using said acquired image set acquired in step d) and said additional image set acquired in step i). In this embodiment at least one additional binary pattern projected onto the portion of said 3D surface may be an inverse comb pattern of the at least one comb pattern.

In another example embodiment, the binary de Bruijn sequence may be comprised of two or more lower order de Bruijn sequences and further comprising:

projecting at least one Gray code or another additional binary pattern onto the portion of the 3D surface;

acquiring an image set of at least a portion of the Gray code or another additional binary pattern with the one or more cameras;

using the image set of the Gray code or another additional binary pattern to subdivide the image set of at least a portion of the pattern of the projected binary de Bruijn sequence into unique regions corresponding to each lower order de Bruijn sequence.

A further understanding of the functional and advantageous aspects of the disclosure can be realized by reference to the following detailed description and drawings.

BRIEF DESCRIPTION OF DRAWINGS

Embodiments of the structured light method will now be described, by way of example only, with reference to the drawings, in which.

DETAILED DESCRIPTION

Figure 1:
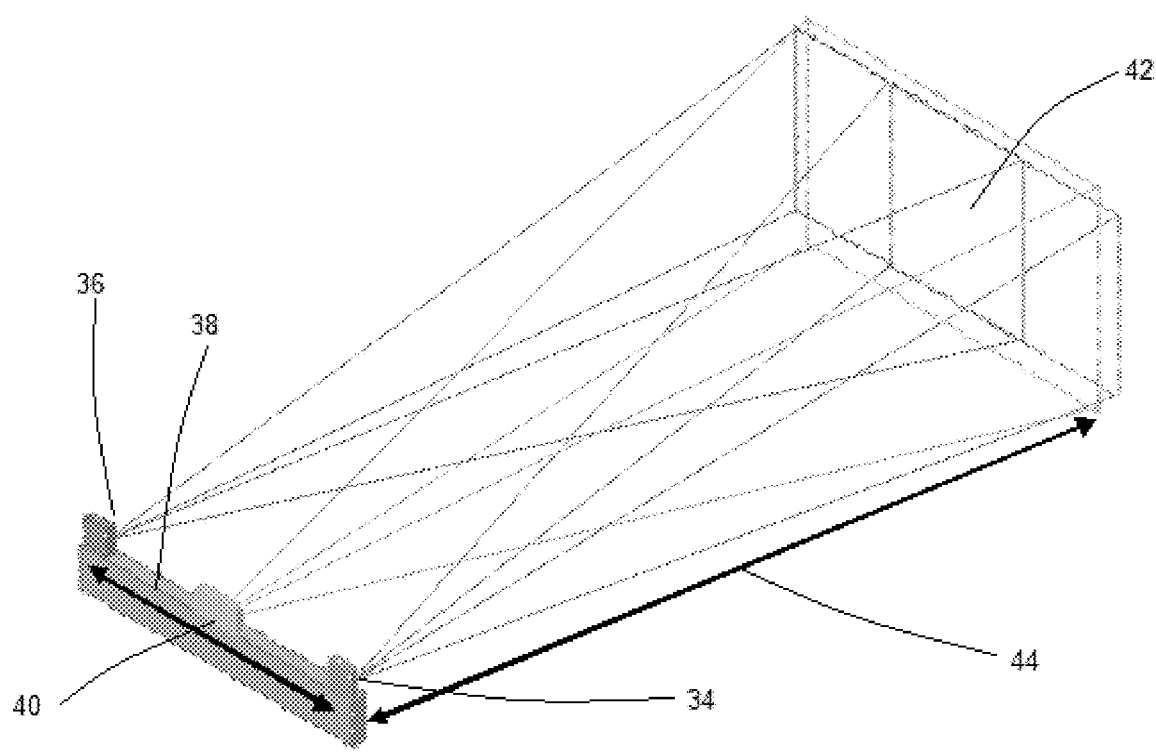
FIG. 1 shows an example stereo camera system used for structured light imaging.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "binocular disparity", or "disparity" in the context of computer vision, refers to a difference in coordinates of similar features within two stereo images, or between an image an reference image. More specifically, disparity refers to the distance between two corresponding pixels in the left and right image of a stereo pair, or between pixels in a single image and a reference image.

As used herein, the phrase "disparity map" refers to the set of disparities calculated between a stereo image pair, or between an acquired image and a reference image in the case of a projector-camera system.

As used herein, the phrase decimation refers to a process by which an acquired image dataset of a region illuminated by a projected pattern is reformatted based on the status and detected locations of the projected pattern elements instead of per-pixel intensity values.

As used herein, the phrase "edge" refers to a boundary between adjacent elements of a pattern.

As used herein, the phrase "transition edge" refers to a boundary between adjacent elements of a pattern having different states.

As used herein, the phrase "non-transition edge" refers to a boundary between adjacent elements of a pattern having common states.

FIG. 1 illustrates an example of a conventional structured light imaging system that employs an uncalibrated light pattern projector 40 and two (or more) spatially separated cameras 34 and 36 to image a 3D target (a system of the first type referenced above). In the simplest example case, camera 36 (on the left hand side of the figure) and camera 34 (on the right side of the figure) are parallel and separated by the baseline 38 and are aligned for imaging a target at a given distance 44 away from the cameras image plane 42. In practical imaging scenarios, the cameras 34 and 36 are typically angled slightly towards one another such that the camera images have maximal overlap at a fixed distance from the projector 40.

The two (or more) cameras 34 and 36 are stereo-calibrated using a calibration method. An example calibration technique is the checkerboard method disclosed by G. Bradski, A. Kaehler, Learning OpenCV: Computer Vision in C++ with the OpenCV Library, O'Reilly Media, Inc., 2013, hereinafter [Bradski 2013], which publication is incorporated herein by reference in its entirety. According to the checkerboard method, the cameras capture images of the same planar checkerboard of known dimensions in various orientations, followed by detecting the corner locations in captured images to infer the relative orientation (i.e. transform) between the two cameras 34 and 36. This transform is used to convert a given binocular disparity map to real-world 3D coordinates, thereby yielding a point cloud of the scene. After the stereo cameras 34 and 36 are calibrated, the projector 40 simply needs to project the patterned image(s) into both cameras' field-of-view (FOV). The projected patterns helps generate correspondences between the left and right images to be found.

In an alternative example embodiment corresponding to the second type of structured light configuration, one (or more) calibrated camera(s) are employed with a calibrated light pattern projector 40. According to this example embodiment, the camera and projector are calibrated to form a calibrated projector-camera system. Methods for calibrating projector-camera systems of this second type are also well known and generally treat the projector as an inverse camera. A non-limiting example of such a method is disclosed by R. Raskar et al. (R. Raskar & P. Beardsley, "A

*self-correcting projector*", Computer Vision and Pattern Recognition, 2001. CVPR 2001, Proceedings of the 2001 IEEE Computer Society Conference on (Vol. 2, pp. II-504), IEEE), which is incorporated herein by reference in its entirety.

Having obtained a suitable calibration transform for the structured light system (whether a type one or type two system), the structured light system can be employed for the detection of a surface profile of a 3D object. Some conventional structured light methods based on spatial neighborhoods utilize de Bruijn sequences as the basis for the projected pattern.

The k-ary de Bruijn sequence B (k, n) of order n and alphabet k is a cyclic sequence of $k^n$ length, in which every possible subsequence of length n is unique.

The de Bruijn image that is commonly implemented in structured light detection systems consists of a de Bruijn sequence of B (k, n) repeated across m projector rows. Accordingly, a first step in conventional surface detection method involves the projection of at least one binary De Bruijn sequence onto the surface, where the de Bruijn pattern is selected to illuminate a region located on the target 3D surface. The pattern is then imaged using the two cameras, and the elements of the de Bruijn patterns are identified in each image. Stereo matching is then performed to calculate a disparity map, which can be processed to obtain reconstructed 3D surface data.

For projector patterns consisting of binary values (e.g. ON and OFF, dark and bright, white and black etc.), the alphabet is k=2. Larger alphabet (k>2) de Bruijn sequences utilize the projection and capture of grayscale or color-coded patterns. The use of larger alphabets allows the scene to be reconstructed with a single projected pattern, making larger alphabets suitable for dynamic scenes. Furthermore, use of larger alphabets enables a lower order pattern to be used, thus relaxing the local smoothness approximation. However, the use of large alphabets comes at the cost of loss of robustness in situations with variable lighting conditions, variable reflectivity of the target (both wavelength and intensity) compared to easily distinguishable binary patterns. Conversely, the use of a small alphabet (e.g. k=2, for binary patterns) can increase robustness to lighting condition, but requires a higher-order de Bruijn sequence, which is less suitable for imaging targets with sharp changes in elevation (i.e. targets that are not smooth).

Figure 2A:
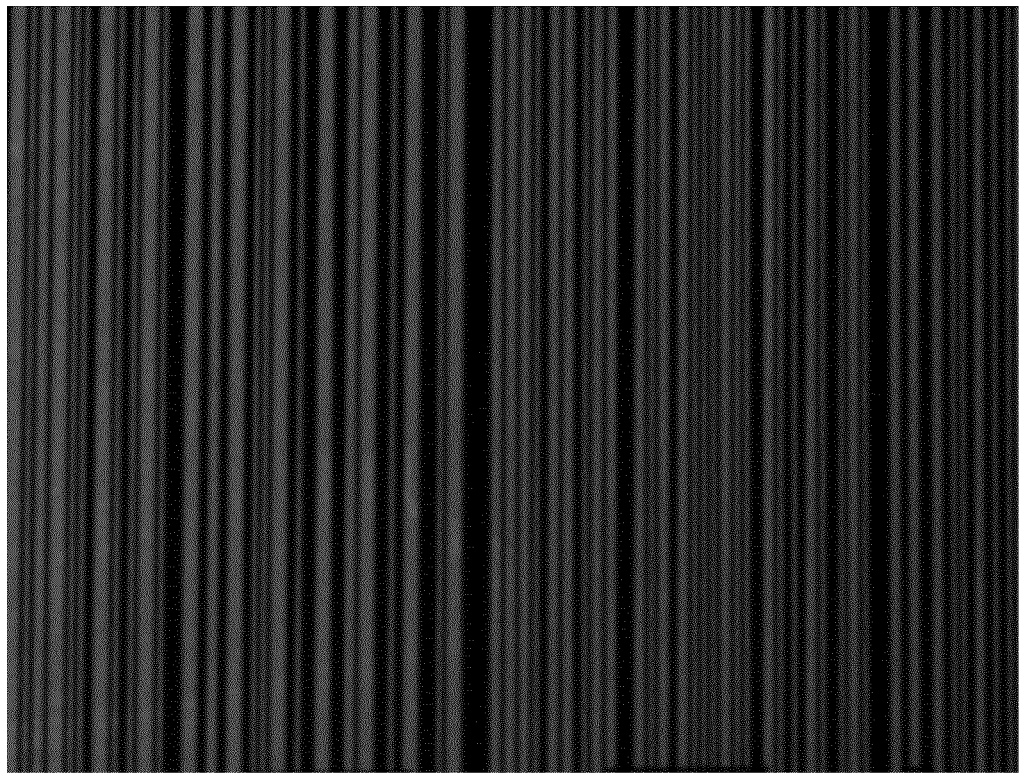
FIG. 2A shows rows of an example binary de Bruijn pattern.
Figure 2B:
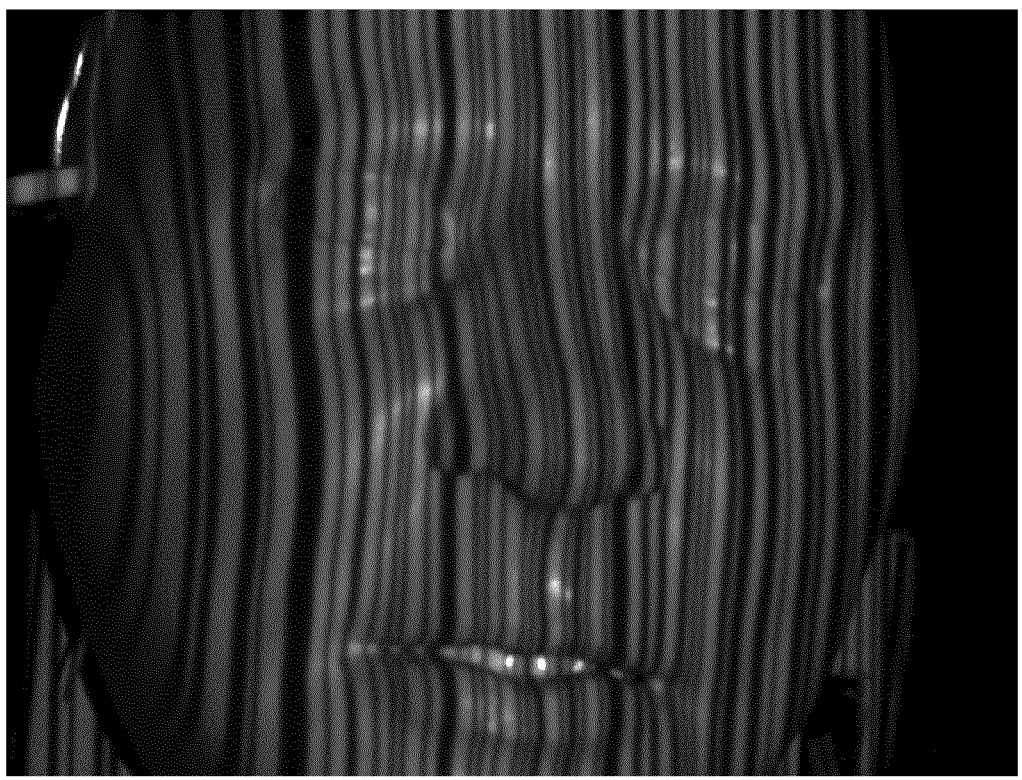
FIG. 2B shows rows of an example binary de Bruijn pattern projected onto a surface having height variations.

In some example implementations, given an alphabet k, a sufficient order n can be selected to fill the entire row of the projector for a desired projection column width. Therefore, according to such an implementation, a fixed relationship exists between the alphabet k and order n given a desired number of projector columns (which defines the resolution of the reconstruction). FIGS. 2A and 2B, show an example of a de Bruijn structured light pattern that is projected across multiple image rows onto a flat (A) and curved (B) surface.

When a binary de Bruijn sequence is employed, with k=2, the different binary values correspond to the white and black state of the projector pixel when it is either fully turned on or off, respectively. In principle, this allows for the unique identification of each projector column with one or more unique IDs (using the n, or more, elements preceding or following it). For example, a binary de Bruijn image may be formed using a de Bruijn sequence of B(2, 9) repeated vertically across m projector rows, with $2^9=512$ sequence values per row. The use of a common pattern among multiple rows is beneficial in that it permits stereo rectified images. Stereo rectification is a process by which the rows of left camera image is aligned to the rows of the right camera image. This facilitates matching between the left and right camera image by only searching in corresponding rows, thus simplifying the search process (i.e. the 2D problem becomes a 1D problem). For example, when searching for a match to a pixel located in row 265 of the left camera, it is only necessary to search row 265 of the right camera to find its match.

When at least one binary de Bruijn sequence is projected, an image of this projection is acquired using at least one camera (with the number and orientation of the cameras being dependent on type of structured light system). In using only these two states, the captured images are less susceptible to color variation in the scene, an issue that is inherent with projecting grayscale or color de Bruijn patterns. For example, a binary (k=2) De Bruijn sequence pattern with order n of 9 or higher can be used to fill 1024 projector columns using a projector column width of two (2) pixels.

In some cases, the number of patterns used can be increased, thereby allowing a reduction in the order of the de Bruijn sequence used. Such an approach can result in an overall reconstruction that is more robust in situations where sharp elevations or large slopes are expected. The use of multiple patterns also enables smaller alphabets to be used (usually binary) which are typically much easier to distinguish than gray levels or different colors.

Referring again to FIGS. 2A and 2B, it is apparent that many sequential (adjacent) elements of the de Bruijn pattern share a common state. For example, referring to FIG. 2A, it is apparent that many edges (locations of boundaries between adjacent elements) of the example de Bruijn sequence are not visible. These invisible edges, referred to herein as "non-transition edges", occur within the contiguous (sequential) stripes having a common white or black state, elements which are henceforth referred to as sequential common-state elements. Such edges can be contrasted with transition edges that occur between adjacent elements that have different states. As can be seen in FIG. 2B, when such a pattern is projected onto a surface having height variations, it can be difficult to accurately determine the non-transition edges of within the contiguous regions associated with the common-state sequential elements. This lack of accuracy in the identification of non-transition edge locations within the common-state sequential elements leads to associated inaccuracies in processing of the detected structured light pattern, such as spatial inaccuracies when performing stereo matching and the generation of a disparity map, which ultimately lead to inaccuracies in the surface data obtained that characterizes the surface profile of the surface.

The present inventors have found that the problems associated with the inability to accurately identify non-transition edges within sequential common-state elements of a structured light pattern may be solved by the projection an additional pattern (or a plurality of such patterns). Such additional patterns are henceforth referred to as binary edge detection patterns, and include transition edges that are spatially aligned with the locations of non-transition edges of the structured light pattern.

Figure 3A:
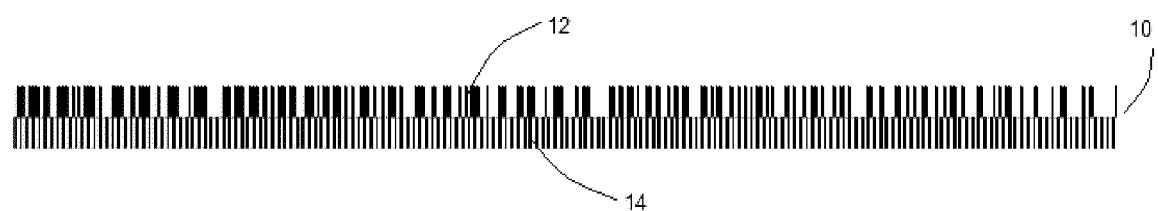
FIG. 3A shows a schematic of the binary de Bruijn sequence of B(2, 9) and the corresponding binary comb pattern sequence, where each stripe of the comb pattern sequence is aligned with a respective an element in the de Bruijn sequence.

FIG. 3A shows an example of a structured light sequence (a binary de Bruijn sequence) along with an example binary edge detection pattern suitable for identifying non-transition edges within the sequential common-state elements of the structured light sequence. As shown in the figure, the projected binary pattern sequence includes a binary de Bruijn pattern 12 (composed of alternating white and black regions) followed by a binary comb pattern 14. The white to black (and black to white) transition edges of the binary comb pattern 14 are spatially aligned with the locations of respective non-transition edges within the corresponding de Bruijn sequence pattern image 12. The binary de Bruijn pattern 12 and the corresponding and spatially aligned binary comb pattern image 14 are sequentially projected to illuminate a region on the 3D surface. As described below, at least a portion of each projected image is acquired by one or more camera(s) of the system. The binary comb pattern is projected such that it overlaps with at least a portion of the target 3D surface that was illuminated by the de Bruijn pattern.

The binary comb pattern may be employed to segment the scene into regions that correspond to the elements of the de Bruijn sequence pattern image 12, thereby allowing the identification of the de Bruijn non-transition edges corresponding to adjacent pattern elements that share a common state with improved accuracy. As described in further detail below, the binary comb pattern is but one example of many different binary edge detection patterns that may be employed with a given structured light pattern.

Figure 4A:
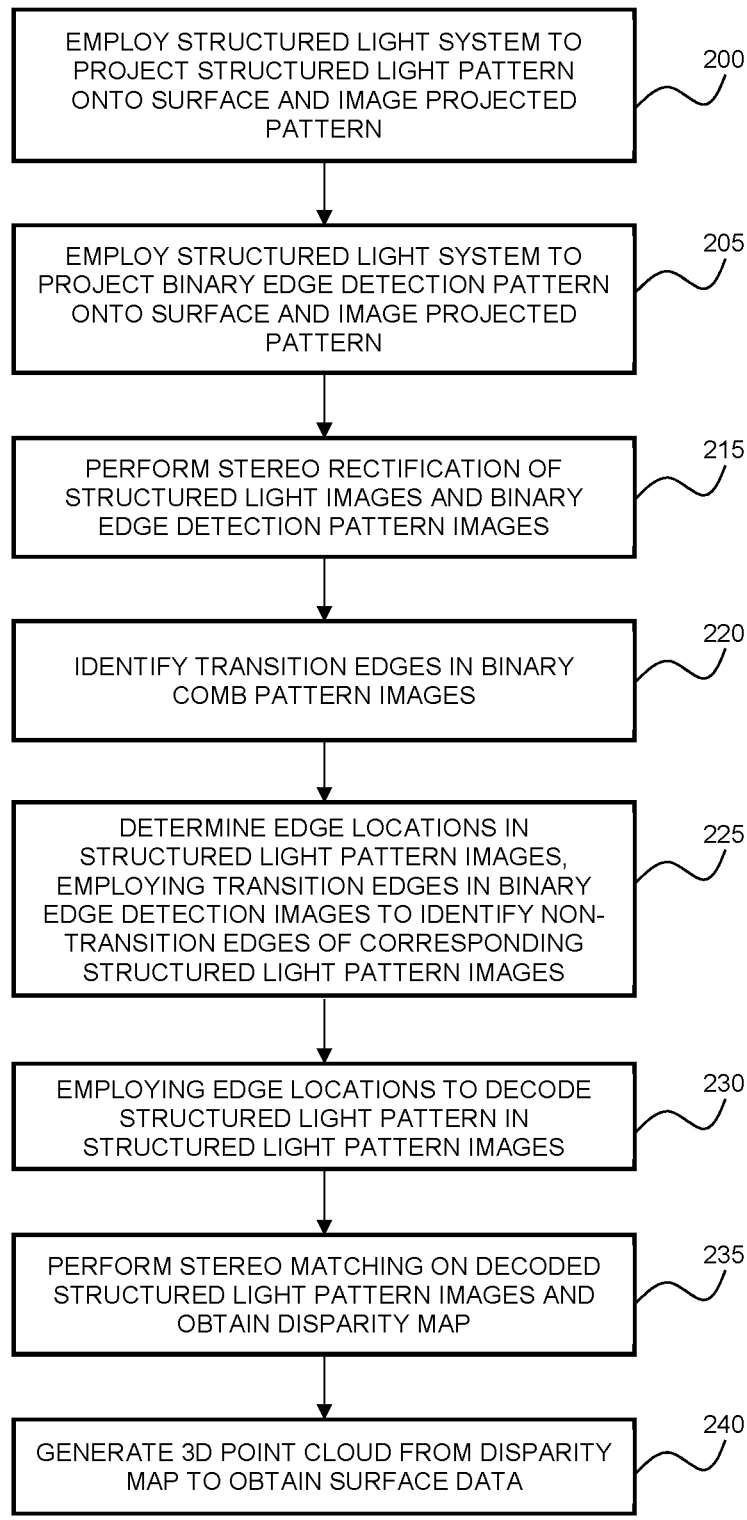
FIG. 4A is a flow chart illustrating an example method of performing structured light detection using a binary edge detection pattern.

Referring now to FIG. 4A, a flow chart is provided that illustrates an example method of performing structured light detection of a surface, in which a structured light pattern is projected along with a binary edge detection pattern, and where the binary edge detection pattern is employed for the detection of non-transition edges between elements of the structured light pattern that have a common state. In step 200, a binary structured light pattern, such as a binary de Bruijn pattern, is projected onto at least a portion of the surface, and the projected binary structured light is imaged with the structured light system. In step 205, a binary edge detection pattern is projected such the edges of the binary edge detection pattern are spatially aligned with the edges of the binary structured light pattern, and the projected binary edge detection pattern is imaged with the structured light system. This process may be performed across multiple rows, in order to scan a desired spatial region of the surface. When imaging over multiple rows, step 200 may be per performed by projecting the structured light pattern onto the multiple rows at the same time, and likewise, step 205 may be per performed by projecting the binary structured light pattern onto the multiple rows at the same time. It will be understood that step 205 may be performed prior to step 200.

As shown at 215, stereo rectification is then performed to align each row of the binary comb pattern images and the binary structured light pattern images respectively captured by the left and right cameras of the structured light system. The stereo rectification is performed such that the subsequent stereo-matching of the binary structured light patterns can be limited to each one-dimensional row instead of a searching a two-dimensional space.

In step 220, the aligned edges of the binary comb pattern images are then found. This can be performed with subpixel approximation, where the two comb images are subtracted from one another and linear interpolation can be used to infer zero crossings [Salvi 2004]. Once the edges of the binary comb patterns are identified, they can be directly used to identify corresponding non-transition edges of the de structured light pattern (thereby decimating the imaged structured light pattern into is constituent elements) since the binary comb edges are aligned to the edges of elements of the structured light pattern sequence.

Figure 4B:
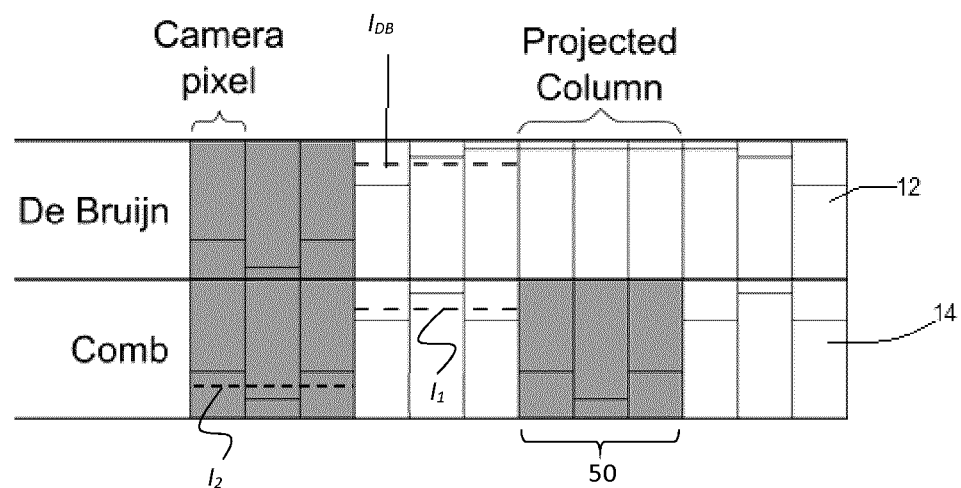
FIG. 4B shows a schematic of an enlarged view of a de Bruijn sequence and a comb. The figure shows how average values are calculated from camera pixel values and used to determine whether an element of de Bruijn sequence is in an ON or OFF state.

The structured light pattern sequence (e.g. the de Bruijn sequence) can then be decoded, as shown in step 230. The decoding process may be understood with reference to FIG. 4B, which shows pixels within a row of an example de Bruijn pattern 12, and pixels of the corresponding binary comb pattern 14, for one of the image sets (left or right). As shown in FIG. 4B, each adjacent edge pair of the binary comb pattern defines a region corresponding to a single element 50 in the de Bruijn sequence 12. Averaging the camera pixel intensity within each element region within the two image columns enables a determination of the state (i.e. black or white) of each element in the de Bruijn pattern. The mean intensity levels of the black and white states of the binary comb image may be computed by averaging the pixel intensities. The average intensity within a given de Bruijn element may then be compared to the black and white state mean intensities of the binary comb image, thereby enabling a determination of the state of the de Bruijn element. For example, if $I_1$ corresponds to the mean intensity of the white elements of the binary comb image, and $I_2$ corresponds to the mean intensity of the black elements of the binary comb image, then if the mean intensity with the de Bruijn element, $I_{db}$, is closer in value to $I_1$ then to $I_2$, then the de Bruijn element is determined to be white, while otherwise, if $I_{db}$ is closer in value to $I_2$ than $I_1$, then the de Bruijn element is determined to be black.

FIG. 4B shows an idealized case where the edges of the projected pattern are aligned to the camera pixel edges. Generally, the projected pattern edges will not be aligned to the camera pixel edges. In these cases, the transition between a black and white projected stripe is not a perfect step but rather has a non-linear profile. Algorithms, such as those described in [Salvi 2004], that provide sub-pixel edge estimation handle these cases by interpolating the position of the stripe transition.

Having identified the transition and non-transition (e.g. visible and invisible) edges in the de structured light images, and decoded the structured light pattern, stereo-matching is then applied to the images, as shown at step 235. According to one example implementation, each edge identified in the left binary de Bruijn image is taken as a reference point, and the subsequence of length n in the de Bruijn (order n) that corresponds to this point is matched to the corresponding n-element subsequence in the right image (or vice versa). If the corresponding sequence is found, the left camera edge is subtracted from the right camera edge (e.g. in units of camera pixels, or other suitable spatial units), which gives the disparity in the images, thereby generating the disparity map.

As shown at step 240, the disparity map is then employed, along with the stereo camera calibration parameters of the system, to convert the disparity values to a three-dimensional point cloud, thereby generating surface data characterizing a surface profile of the imaged surface region. For example, through the stereo rectification algorithm implemented in the OpenCV toolbox, the camera calibration parameters can be used to generate a perspective transformation (4×4 matrix) which directly maps disparity to depth.

Convention structured light detection systems typically employ one of two two system types; 1) calibrated stereo cameras with an uncalibrated projector, and 2) a calibrated camera with a calibrated projector. The calibration process of the first system type is better suited to medical applications than the latter. This system type is therefore used in various illustrative example embodiments of the present disclosure that relate to medical procedures. However, the example embodiments disclosed herein may alternatively be implemented using the second type of structured light systems. In general, it will be understood that the example embodiments described herein are intended to provide non-limiting example applications that can be extended to a wide variety of applications using either system type.

Figure 4C:
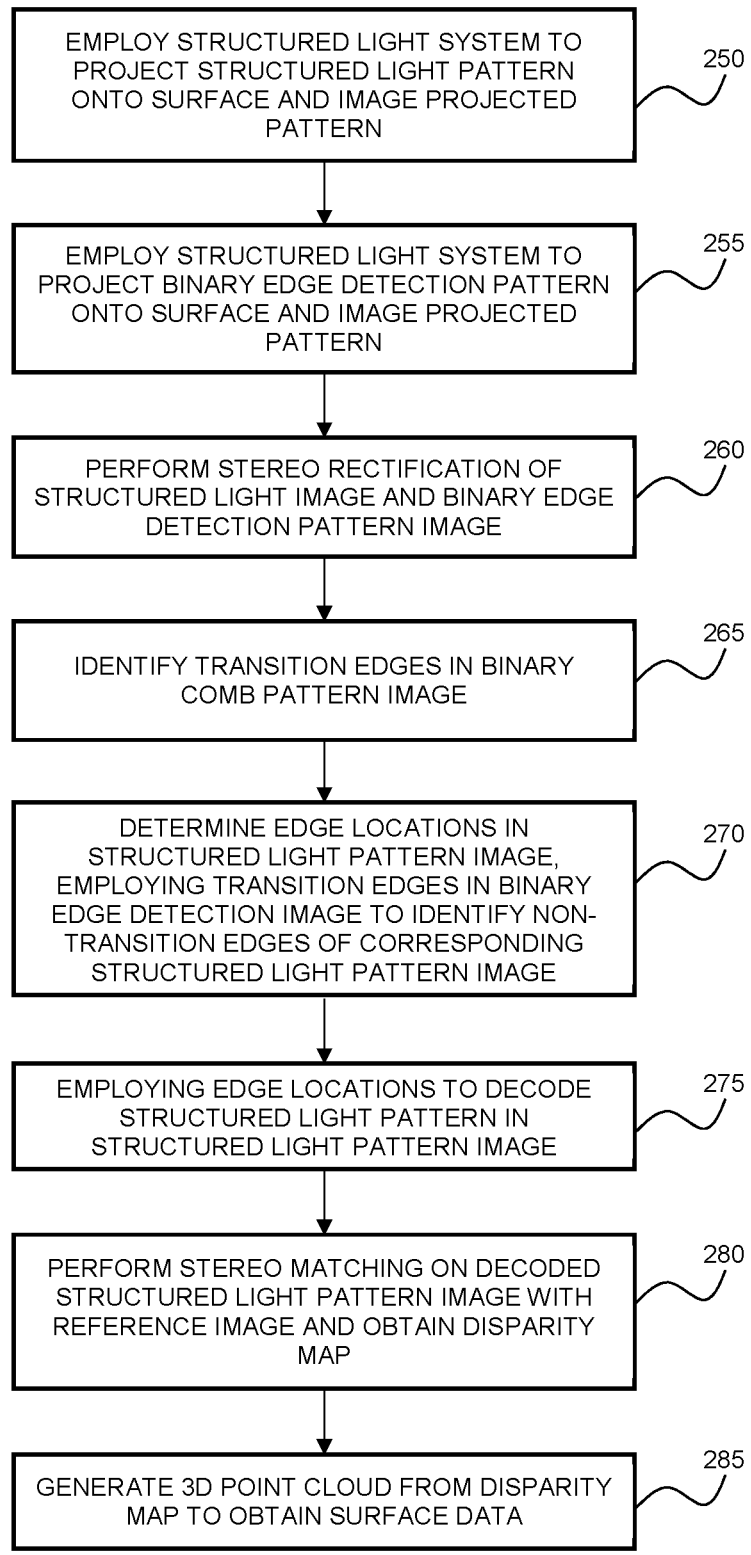
FIG. 4C is a flow chart illustrating an alternative example method of performing structured light detection using a binary edge detection pattern.

FIG. 4C is a flow chart illustrating an example implementation of the aforementioned method for a structured light system that employs a calibrated camera and projector. In steps 250 and 255, the structured light pattern and the binary edge detection pattern are sequentially projected by the projector such that the locations of the elements of the projected structured light pattern are spatially aligned with the locations of the elements of the projected binary edge detection pattern, and images are collected with the camera. Stereo rectification of the images is performed in step 260. Transition edges in the binary comb pattern image are identified in step 265, for example, using the methods described above. In step 270, the transition edges are used to identify corresponding non-transition edges of the projected structured light pattern (and optionally also transition edges of the projected structured light pattern). The structured light pattern is then decoded, as shown in step 275. In step 280, the decoded structured light pattern image is stereo matched to a reference image obtained with a reference surface (e.g. a flat surface), providing a disparity map. As shown in step 285, the disparity map may be employed to generate surface data, e.g. in the form of a 3D point cloud, thereby providing a reconstruction of the imaged surface. Example methods of generating a disparity map from a decoded structured light image and a reference image are shown in D. Lanman et al., Build Your Own 3D Scanner: 3D Photography for Beginners (SIGGRAPH 2009 Course Notes), 2009.

The preceding example embodiments therefore address the aforementioned problems associated with structured light detection by employing a spatio-temporal binary sequence that employs as few a one binary structured light pattern and one binary edge detection pattern. The example systems and methods disclosed herein may be beneficial in generating disparity measurements with sub-pixel accuracy.

As described above, previous structured light detection techniques typically only use the de Bruijn sequence when projecting the pattern. The inclusion of a projected binary edge detection pattern (e.g. a binary comb) provides the additional information for decimating the de Bruijn image into its constituent elements, making matching between the left and right images much simpler. Additionally, the projection of the binary edge detection pattern enables the edges of the elements within the de Bruijn code to be calculated with sub-pixel accuracy, for example, by finding zero crossings of the second derivative. While methods such as cross-correlation have been used to generate correspondences between the acquired images, they may be less robust at imaging in an environment where the lighting and surface color/reflectivity can vary.

In the example embodiment presented in FIG. 3A, and in many of the example embodiments described and illustrated herein, the projected binary edge detection pattern (and the associated de binary structured light pattern) has equal width columns of white and black elements. However, it will be understood that these example embodiments are not intended to be limiting, and that the various example embodiments described herein may alternatively be implemented without this requirement, provided that the edges of the binary comb pattern are spatially aligned with the corresponding edges of the de Bruijn pattern.

It will be understood that the binary comb pattern provides one non-limiting example of a wide array of potential binary edge detection patterns that may be employed according to the example embodiments described herein.

Indeed, since several adjacent regions of a binary structured light pattern (e.g. a de Bruijn pattern sequence) already alternate between white and black and thus include transition edges among elements, these elements do not require the presence of transitions edges in a binary edge detection pattern. In other words, it is not necessary in general to use a full binary comb pattern, as a subset of edges can be found from the binary structured light pattern directly.

Accordingly, the binary comb pattern can be understood as a special case of a binary edge detection pattern that may be used generically with any binary structured light pattern, independent of the specific element sequence of the structured light pattern. If a binary comb pattern is projected, then the transition edges of the binary comb pattern may be employed to identify all of the edges of the structured light pattern or only a subset of the edges of the structured light pattern, such as the subset corresponding to the non-transition edges of the structured light pattern. On the other hand, and other binary edge detection patterns may be used that are specific to a given structured light pattern.

Figure 3B:
FIG. 3B shows an example embodiment of a de Bruijn sequence and a complementary binary pattern, wherein the complementary binary pattern is an aperiodic binary pattern.

FIG. 3B shows a non-limiting example of such a pattern in which the upper row is the de Bruijn sequence and second lower row is the new pattern. In this embodiment only regions of the binary pattern corresponding to contiguous regions of the de Bruijn sequence include transitions for edge detection (e.g. as per the "comb architecture" described above). This is a specific implementation of an example embodiment a binary comb pattern is provided in the regions over which the structured light sequence is contiguous.

Accordingly, in some example embodiments, a binary edge detection pattern used to decode a structured light pattern may be a binary comb. In another example embodiment, the binary edge detection pattern includes sufficient transition edges to decode the structured light pattern. In another example embodiment, the binary edge detection pattern includes a minimum number of transition edges to decode the structured light pattern. In one example embodiments, a binary edge detection pattern used to decode a structured light pattern may include a binary comb pattern within at least a sub-sequence of the binary edge detection pattern, and wherein the remainder of the binary edge detection pattern includes sufficient transition edges to decode the structured light pattern.

It will be understood that the binary edge detection pattern need not include transition edges that correspond to all non-transition edges of the structured light pattern. In some example embodiments, the binary edge detection pattern may include transition edges suitable for identifying only a subset of the non-transition edges of the structured light pattern, such as one or more non-transition edges. In such cases, the remaining non-transition edges may be identified using other means, such as by interpolation.

It will also be understood that the binary edge detection pattern may include more transition edges than are necessary to identify the non-transition edges of the structured light pattern. A binary comb pattern is an example of such a binary edge detection pattern.

In some example embodiments, a plurality of edge detection patterns may be sequentially projected in order to decode the structured light pattern. For example, in one example embodiment two binary comb patterns are sequentially employed, where the two binary comb patterns are complementary to each other (e.g. with reversed states) in order to avoid degeneracy.

In such an example embodiment, three patterns are projected in sequence: the binary structured light (e.g. de Bruijn) pattern of white and black columns, followed by a binary comb pattern, and an additional binary pattern that is the inverse of this comb image, both of which are composed of vertical white and black columns of equal width. The white-to-black transition edges in all three images are aligned. The latter two complementary images consist of alternating black and white columns, thereby segmenting the scene into regions that correspond to single elements in the de Bruijn sequence.

Figure 5A:
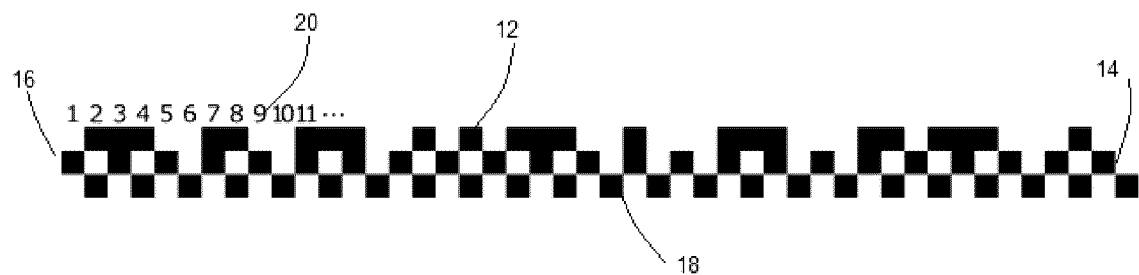
FIG. 5A shows a schematic of an enlarged view of the de Bruijn sequence and the matching complementary comb sequences, where any subsequence of 9 elements of the de Bruijn sequence are unique.
Figure 5B:
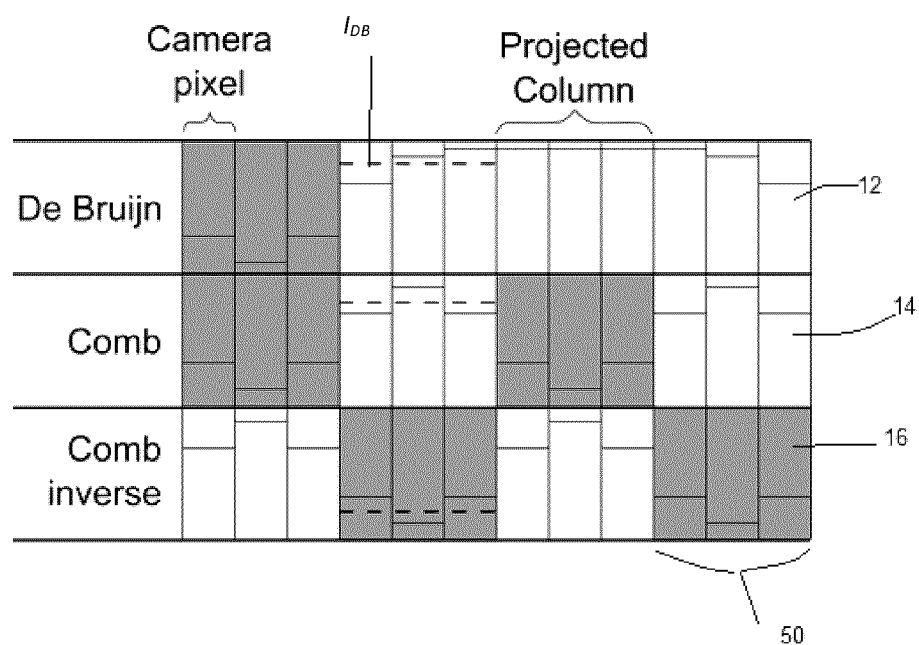
FIG. 5B shows a schematic of an enlarged view of the de Bruijn sequence and the matching complementary comb sequences, where any subsequence of 9 elements of the de Bruijn sequence are unique.

FIGS. 5A and 5B illustrate such an embodiment, showing a structured light pattern 16 consisting of the de Bruijn pattern 12 in sequence together with both the comb pattern image 14 and its complementary comb inverse pattern 18. In this instance, any nine element subsequence 20 is unique. By using the two complementary comb pattern images 14 and 18, the de Bruijn image pattern sequence can be decimated, providing a better sub-pixel estimate of edges compared to finding zero crossing of the second derivative as done when only projecting a single comb pattern, as disclosed in [Salve 2004], which is incorporated herein by reference in its entirety.

It will be understood that the use of a complementary binary edge detection pattern (with inverted states relative to a given binary edge detection pattern) may be employed with binary edge detection patterns other than the binary comb pattern. For example, the inverse of the non-uniform comb pattern shown in FIG. 3B may similarly be projected in order to decimate the de Bruijn sequence more accurately.

Figures 5C, 6:
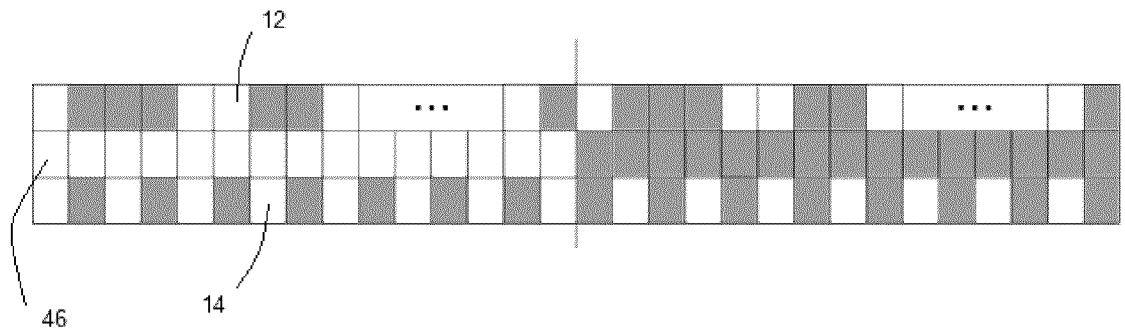
FIG. 5C shows an example de Bruijn sequence, a Gray code, and a binary comb.
FIG. 6 shows a table presenting the relation between the order of de Bruijn sequence, the number of columns of the projected comb and the number of Gray codes for different subpixel interpolation methods that can be used to subdivide the image. In the table, C is the number of columns in the projected comb pattern sequence and $n_g$ is the number of Gray codes used to subdivide the images.

In another example embodiment, a binary de Bruijn sequence pattern 12, a comb pattern 14 and one or more Gray code or other binary codes 46 may be employed, as shown in FIG. 5C. The additional code may aids in preventing violation of the local smoothness assumption, by subdividing the image in to smaller regions which can be spanned by a lower order de Bruijn pattern. As an example, an image with a width of 512 columns in the projected comb would require a binary de Bruijn pattern of order 9 to span the entire image. If a Gray or binary code (256 0's followed by 256 1's: 00000 . . . 000|111111 . . . 111) is used to subdivide the image of the projected pattern, then a binary de Bruijn of order 8 could be used to span each half image. This process further minimizes the subset that is being analyzed for generating a positive match between images, which in turn reduces the chance that the local smoothness assumption will be violated.

The table provided in FIG. 6 illustrates how the total number of projected patterns 26 scales as function of the order 24 of the de Bruijn sequence, the sub-pixel interpolation method 22 used to decimate the de Bruijn sequence. In the table, C 30 is the number of columns in the projected comb and $n_g$ 28 is the number of sequentially projected Gray codes used to subdivide the image so that de Bruijn sequences of lower order may be used. Additional projected patterns of a gray/binary code that subdivide the image can be used to further reduce the required order of the de Bruijn sequence.

The following non-limiting examples of alternative binary edge detection patterns may be utilized in the structured light detection embodiments described herein. It will be understood that many alternative binary edge detection patterns, or sets of binary edge detection patterns, may also be employed.

Two pattern sequence:
  a. comb image with the de Bruijn sequence
Three pattern sequences:
  a. comb image and inverse comb image with the de Bruijn sequence
  b. comb and Gray image with the de Bruijn sequence
Four pattern sequences:
  a. comb, comb inverse and gray1 images with the de Bruijn sequence Five pattern sequence:
  a. comb, comb inverse, gray1 and gray1 inverse images with the de Bruijn sequence While many of the example embodiments disclosed herein employ the use of binary edge detections for the detection of edges among contiguous elements of a binary structured light pattern, it will be understood that the present example embodiments may be applied to non-binary structured light patterns, such as de Bruijn patterns having an alphabet of k>2. For example, a binary edge detection pattern may be employed for the detection of edges among contiguous elements of a greyscale structured light pattern and/or a colour structured light pattern.

Figure 7:
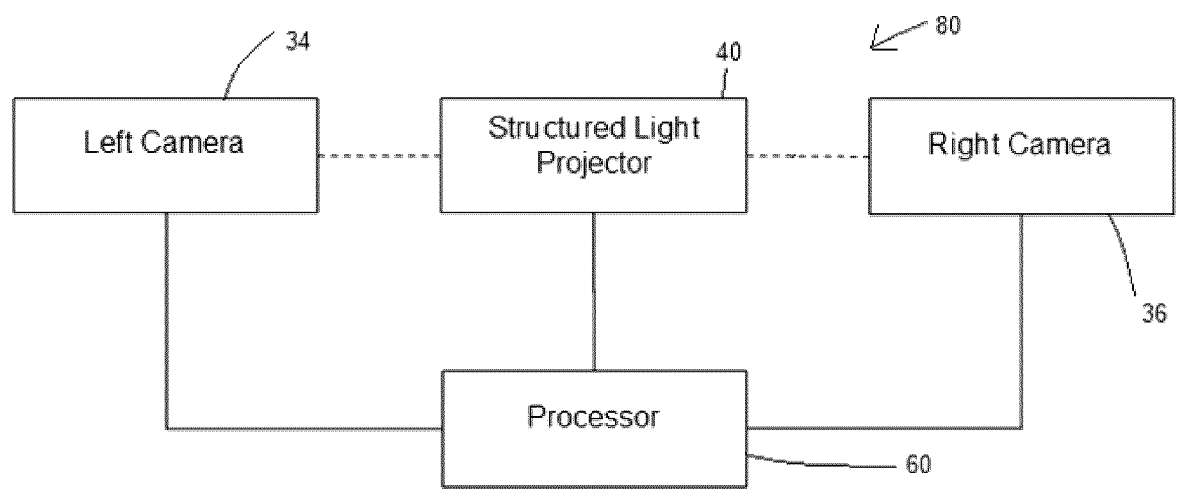
FIG. 7 shows a block diagram of an example system 80 for performing the present example methods of obtaining a structured light reconstruction of a 3D surface.

FIG. 7 shows a block diagram of a system 80 which uses the present method for obtaining a structured light reconstruction of a three dimensional (3D) surface. Left camera 34 and right camera 36 and structured light projector 40 are connected to a processor unit 60 so they are under processor control. The dashed connection lines between projection system 40 and cameras 34 and 36 indicate optional synchronization links between the projection system 40 and cameras 34 and 36 for the purpose of synchronization the projection and acquisition of the images. Alternatively, the processor 60 can synchronize the projection and acquisition directly.

Figure 8:
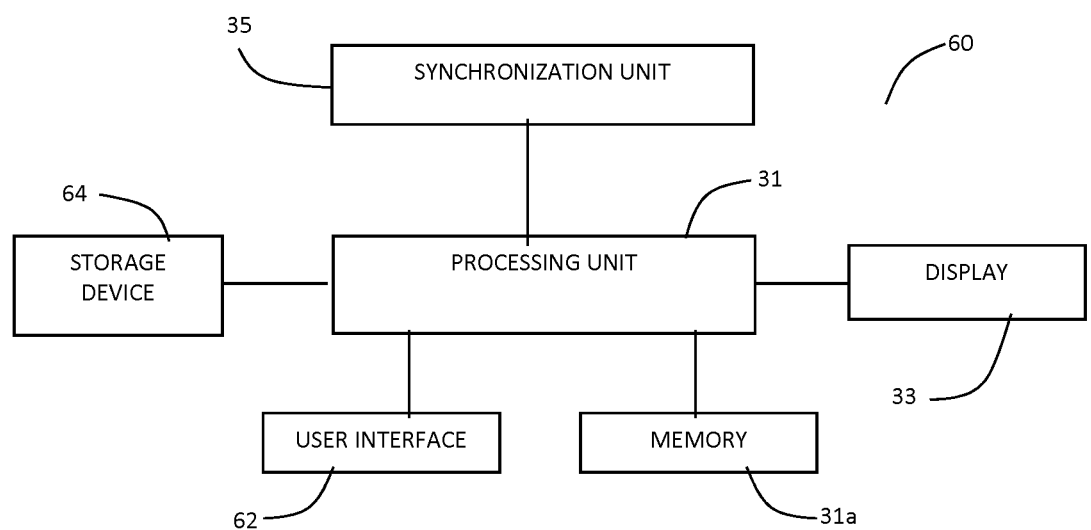
FIG. 8 is a block diagram showing an example implementation of a control and processing unit that may be incorporated as a component of the example structured light system shown in FIG. 7.

FIG. 8 shows an example embodiment of control and processing unit 60, which may include computer hardware such as a processing unit 31 (e.g. one or more processors) and associated memory 31 containing one or more computer programs to control the operation of the system, where processing unit 31 is in communication with a user interface unit 62 and display 33. In one example, the control and processing unit 60 may be a computing system such as a personal computer or other computing device, for example in the form of a computer workstation, incorporating a hardware processor and memory, where computations are performed by the processor in accordance with computer programs stored in the memory to carry out the methods such as initiation of structured light imaging and reconstruction of acquired images into surface topology. For example, the processor can be a central processing unit or a graphical processing unit, or a combination of a central processing unit or graphical processing unit. Data from these methods may be stored on a device storage unit 64.

The instructions to control structured light projector 40 and/or the cameras 34 and 36 may be generated by processing unit 31. Alternatively, control and processing unit 60 may contain a synchronization unit 35, which may be used to output various instructions to the structured light projector 40 and/or the cameras 34 and 36. For example, the synchronization unit 35 could take the form of one or more additional processors, which may be linked to processing unit 31 via serial communication or another connection method (WI-FI, USB, Ethernet, Bluetooth etc.). Alternatively, the synchronization unit 35 may be an analogue or digital data acquisition (DAQ) card. The instructions can be transmitted to the structured light projector 40 and/or cameras 34 and 36 in the form of various digital and/or analog communication methods and protocols, such as, for example, electrical, optical, acoustical or other methods.

In one embodiment, control and processing unit 60 includes a general purpose computer or any other hardware equivalents. Thus, the system may include at least one processor (CPU/microprocessor), a memory, which may include random access memory (RAM), one or more storage devices (e.g., a tape drive, a floppy drive, a hard disk drive or a compact disk drive), and/or read only memory (ROM), and various input/output devices (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, 6-degree input device based on the position tracking of a handheld device, and the like, and/or a microphone for capturing speech commands, etc.). The control and processing unit 60 may also be implemented as one or more physical devices that are coupled to the CPU through a communication channel. For example, the control and processing unit 60 can be implemented using application specific integrated circuits (ASIC). Alternatively, control and processing unit 60 can be implemented as a combination of hardware and software, where the software is loaded into the processor from the memory or over a network connection. In one embodiment, control and processing unit 60 (including associated data structures) of the present disclosure can be stored on a computer readable medium, e.g., RAM memory, magnetic or optical drive or diskette and the like.

It will be appreciated that the methods disclosed herein may be implemented on existing projector/camera(s) systems, such that computer controllers interfaced with the projector and camera(s) may be retrofitted and programmed with instructions to perform the various methods.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks, (DVDs), etc.), among others. The instructions can be embodied in digital and analog communication links for electrical, optical, acoustical or other forms of propagated signals, such as carrier waves, infrared signals, digital signals, etc. A machine readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.). As used herein, the phrases "computer readable material" and "computer readable storage medium" refers to all computer-readable media, except for a transitory propagating signal per se.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's).

The processing unit 31 is programmed with instructions for processing the acquired images, for example, as noted above this may include:

stereo rectifying acquired images based on calibration parameters which include extrinsic parameters that describe the camera motion around a static scene and intrinsic parameters which are camera parameters that are internal and fixed to a particular camera/digitization setup (intrinsic parameters include parameters such as geometric lens distortion, focal length and transforms which map the camera frame to the pixel coordinates);

calculating the position of projected edges within the comb function with subpixel accuracy as disclosed in Salvi 2004;

decimating the de Bruijn sequence into its constituent elements using the comb image(s);

determining whether constituent elements of the de Bruijn sequence are in an ON (1) or OFF (0) state;

generating matches between left and right images based on the decimated de Bruijn sequence;

calculating a disparity map based on the generated matches; and generating a 3d point cloud from the disparity map using calibration parameters rendering the 3d point cloud.

Figure 9A:
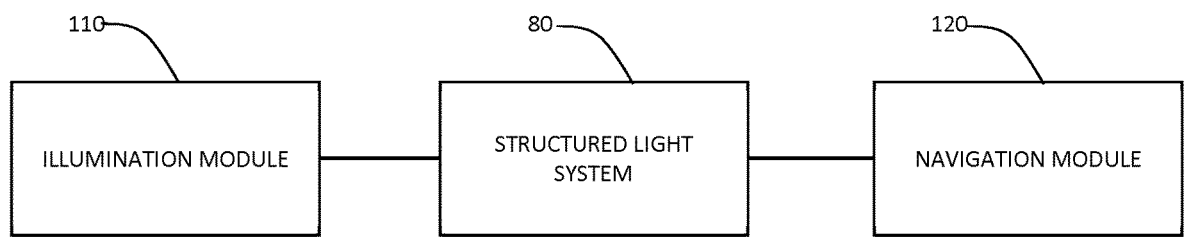
FIG. 9A is a block diagram showing an example composite system incorporating a structured lighting system an illumination module, and a navigation/tracking module.
Figure 9B:
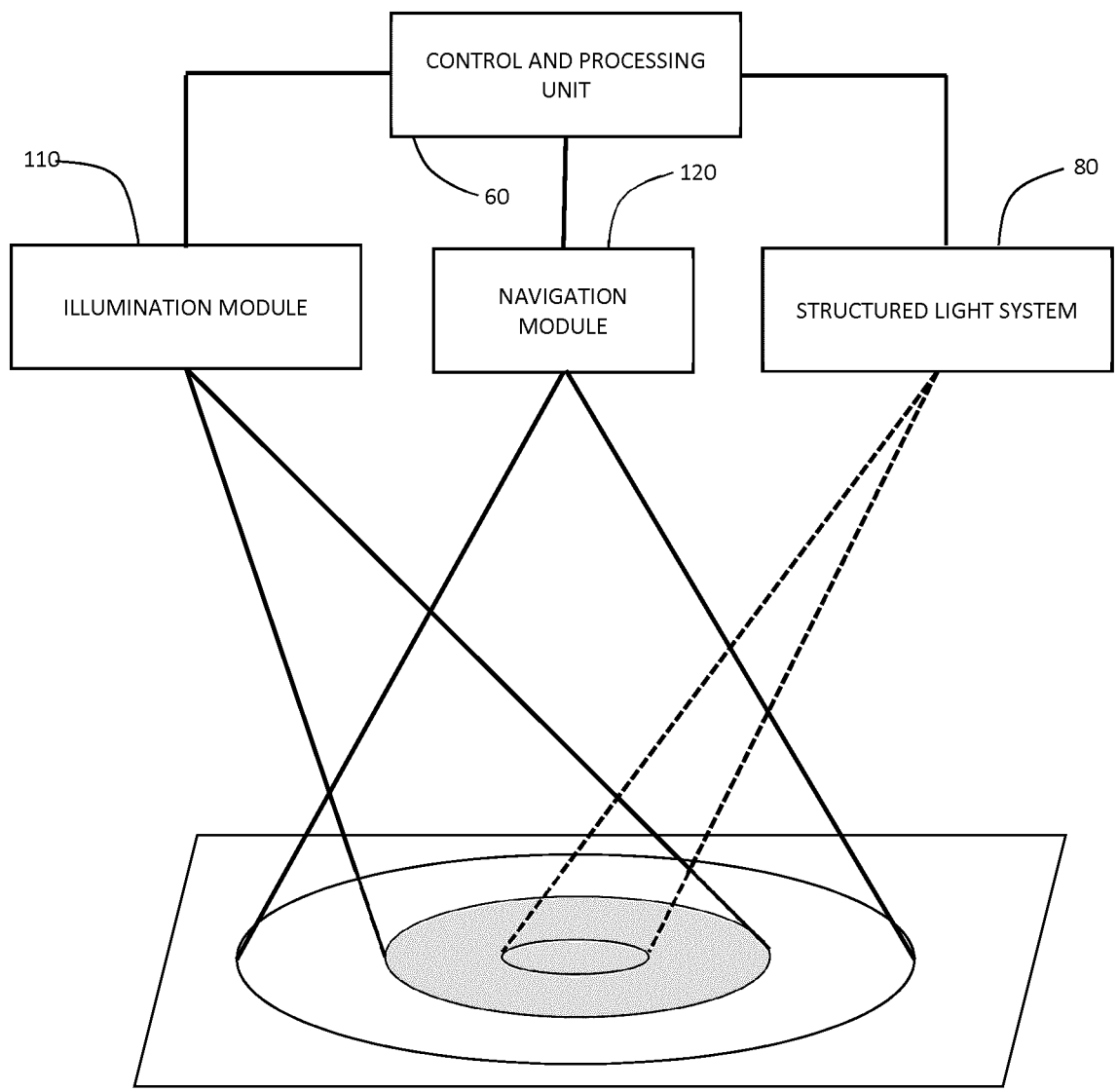
FIG. 9B is a block diagram showing an example composite system incorporating a structured light system, an illumination module, and a navigation/tracking module, which are controlled by a control and processing unit.
Figure 10:
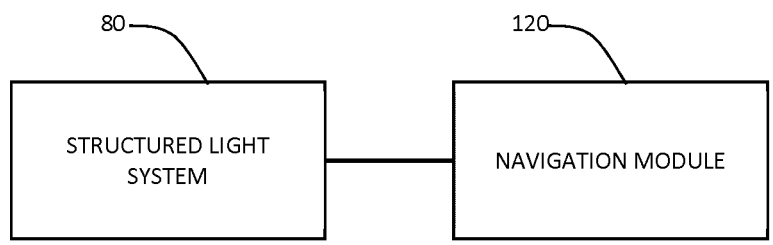
FIG. 10 shows an example composite system in which a structured light system is integrated with a navigation/tracking module 120.

The system and method for obtaining a structured light reconstruction of a 3 dimensional (3D) surface disclosed herein may be integrated into surgical navigation systems which includes integrated illumination. A non-limiting exemplary surgical navigation system is disclosed in United States Patent Publication No. 2015/0300816-A1, which is incorporated herein by reference in its entirety. FIGS. 8A and 8B of United States Patent Publication No. 2015/0300816-A1 show three (3) major subsystems (navigation/tracking module 50, illumination module 10 and optical topology detection module 20). Integration of the present structured light system into the systems of FIGS. 8A and 8B of United States Patent Publication No. 2015/0300816-A1 may involve replacing optical topology detection module 20 in the later publication with the present structured light system 80 comprised of projector 40, cameras 34 and 36 and processor 60 as shown in FIGS. 9A and 9B of the present application, with the illumination module 10 and navigation module 50 of US Publication No. 2015/0300816-A1 being renumbered modules 100 and 120 respectively in present FIGS. 9A and 9B. In addition, the present structured light system 80 may be integrated with the with optical topology detection module 120 (i.e. without the illumination module) as shown in FIG. 10.

Once the 3D surface has been reconstructed, it can be used for a number of different applications, including but not limited to: visually displayed to a user; registration to other 3D datasets (CT, MRI, Ultrasound based 3D reconstructions); registration to other structured light 3D reconstructions acquired at earlier time points; and registration to other 3D CAD (computer aided design) models.

It will be understood that the example embodiments of the present disclosure may be applied to a wide variety of applications, including medical applications and non-medical applications. Indeed, many of the example embodiments described herein may facilitate high-speed, real-time (or near-real time) applications in many different areas. Non-limiting example applications include: real time human computer interaction where objects or people within a target area could be tracked; automated inspection on high speed assembly lines; robotics (medical or otherwise) for guiding machining or cutting of objects with active feedback on how the target is changing during the machining process; security applications such as facial recognition; and gait analysis for rehabilitation, athletics or security.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method for obtaining structured light reconstruction of a 3D surface using a structured light system comprising a projector, and a first camera and a second camera, the method comprising:
    employing the projector to project a structured light pattern onto the 3D surface;
    acquiring, with the first camera and the second camera, respective structured light images of the projected structured light pattern;
    employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein transition edges correspond to boundaries between adjacent elements having different states, and wherein non-transition edges correspond to boundaries between adjacent elements having a common state;
    acquiring, with the first camera and the second camera, respective binary edge detection images of the projected binary edge detection pattern;
    processing each binary edge detection image to identify, within each binary edge detection image, locations of the transition edges;
    determining edge locations of elements within the structured light images, wherein the locations of the transition edges of the binary edge detection images are employed to identify corresponding non-transition edges within the respective structured light images;
    employing the edge locations within the structured light images to decode the structured light pattern within the structured light images;
    performing stereo matching of the decoded structured light images and obtaining a disparity map; and
    generating a reconstruction of the 3D surface based on the disparity map.

2. The method according to claim 1 wherein the structured light pattern is a binary structured light pattern.

3. The method according to claim 1 wherein the binary edge detection image comprise a binary comb pattern aligned with at least two adjacent elements of the structured light pattern that have a common state.

4. The method according to claim 1 wherein the binary edge detection pattern is a binary comb pattern.

5. The method according to claim 1 wherein the binary edge detection pattern includes transition edges that respectively correspond to each non-transition edge of the structured light pattern.

6. The method according to claim 1 wherein the binary edge detection pattern includes transition edges that respectively correspond to a subset of the non-transition edges of the structured light pattern.

7. The method according to claim 1 wherein the binary edge detection pattern is a first binary edge detection pattern and the binary edge detection images are first binary edge detection images, the method further comprising:
    employing the projector to project an additional binary edge detection pattern onto the 3D surface and acquiring, with the first camera and the second camera, respective additional binary edge detection images of the projected additional binary edge detection pattern;
    wherein the additional binary edge detection pattern is projected such that the elements of the projected additional binary edge detection pattern are spatially aligned with the elements of the projected structured light pattern, and such that a plurality of transition edges of the additional binary edge detection pattern are respectively aligned with non-transition edges of the projected structured light pattern; and
    wherein locations of transition edges determined in the additional binary edge detection images are employed to identify corresponding non-transition edges within the respective structured light images.

8. The method according to claim 7 wherein the additional binary edge detection pattern is an inverse of the first binary edge detection pattern.

9. The method according to claim 8 wherein the first binary edge detection pattern comprises a binary comb pattern.

10. The method according to claim 8 wherein the first binary edge detection pattern is a binary comb pattern.

11. The method according to claim 1 wherein the structured light pattern is a de Bruijn pattern.

12. The method according to claim 11 wherein the de Bruijn pattern is a binary de Bruijn pattern.

13. The method according to claim 11 wherein the de Bruijn pattern has an alphabet greater than two.

14. The method according to claim 12 wherein the projected binary de Bruijn pattern comprises two de Bruijn patterns that are projected in a common row, the method further comprising:
    employing the projector to project at least one Gray code the 3D surface such that the Gray code pattern is spatially aligned with the common row;
    acquiring, with the first camera and the second camera, respective Gray code images of the projected Gray code pattern;
    employing the Gray code images to subdivide the projected binary de Bruijn pattern into regions respectively corresponding to the two de Bruijn patterns.

15. A method for obtaining structured light reconstruction of a 3D surface using a structured light system comprising a projector and a camera, the method comprising:
    employing the projector to project a structured light pattern onto the 3D surface;
    acquiring a structured light image of the projected structured light pattern with the camera;
    employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein the transition edges correspond to boundaries between adjacent elements having different states, and the non-transition edges correspond to boundaries between adjacent elements having a common state;

acquiring a binary edge detection image of the projected binary edge detection pattern with the camera;

processing the binary edge detection image to identify locations of the transition edges;

determining edge locations of elements within the structured light image, wherein the locations of the transition edges of the binary edge detection image are employed to identify corresponding non-transition edges within the structured light image;

employing the edge locations within the structured light image to decode the structured light pattern within the structured light image;

performing stereo matching of the decoded structured light image with a reference and obtaining a disparity map; and generating a reconstruction of the 3D surface based on the disparity map.

16. The method according to claim 15 wherein the structured light pattern is a binary structured light pattern.

17. The method according to claim 15 wherein the binary edge detection images comprise a binary comb pattern aligned with at least two adjacent elements of the structured light pattern that have a common state.

18. The method according to claim 15 wherein the binary edge detection pattern is a binary comb pattern.

19. The method according to claim 15 wherein the binary edge detection pattern includes transition edges that respectively correspond to each non-transition edge of the structured light pattern.

20. The method according to claim 15 wherein the binary edge detection pattern includes transition edges that respectively correspond to a subset of the non-transition edges of the structured light pattern.

21. The method according to claim 15 wherein the binary edge detection pattern is a first binary edge detection pattern and the binary edge detection image is a first binary edge detection image, the method further comprising:

employing the projector to project an additional binary edge detection pattern onto the 3D surface and acquiring, with the camera, an additional binary edge detection image of the projected additional binary edge detection pattern;

wherein the additional binary edge detection pattern is projected such that the elements of the projected additional binary edge detection pattern are spatially aligned with the elements of the projected structured light pattern, and such that a plurality of transition edges of the additional binary edge detection pattern are respectively aligned with non-transition edges of the projected structured light pattern; and wherein locations of transition edges determined in the additional binary edge detection image are employed to identify corresponding non-transition edges within the structured light image.

22. The method according to claim 21 wherein the additional binary edge detection pattern is an inverse of the first binary edge detection pattern.

23. The method according to claim 22 wherein the first binary edge detection pattern comprises a binary comb pattern.

24. The method according to claim 22 wherein the first binary edge detection pattern is a binary comb pattern.

25. The method according to claim 15 wherein the structured light pattern is a de Bruijn pattern.

26. The method according to claim 25 wherein the de Bruijn pattern is a binary de Bruijn pattern.

27. The method according to claim 25 wherein the de Bruijn pattern has an alphabet greater than two.

28. The method according to claim 26 wherein the projected binary de Bruijn pattern comprises two de Bruijn patterns that are projected in a common row, the method further comprising:

employing the projector to project at least one Gray code the 3D surface such that the Gray code pattern is spatially aligned with the common row;

acquiring, with the camera, respective Gray code images of the projected Gray code pattern;

employing the Gray code image to subdivide the projected binary de Bruijn pattern into regions respectively corresponding to the two de Bruijn patterns.

29. A system for obtaining structured light reconstruction of a 3D surface, the system comprising:

a projector configured to project patterns onto a surface;

a first camera and a second camera, wherein the first camera and the second camera are oriented to image the patterns projected by the projector; and computer hardware operatively coupled to said projector, said first camera and said second camera, wherein said computer hardware comprises memory coupled with one or more processors to store instructions, which when executed by the one or more processors, causes the one or more processors to perform operations comprising:

employing the projector to project a structured light pattern onto the 3D surface;

acquiring, with the first camera and the second camera, respective structured light images of the projected structured light pattern;

employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein transition edges correspond to boundaries between adjacent elements having different states, and wherein non-transition edges correspond to boundaries between adjacent elements having a common state;

acquiring, with the first camera and the second camera, respective binary edge detection images of the projected binary edge detection pattern;

processing each binary edge detection image to identify, within each binary edge detection image, locations of the transition edges;

determining edge locations of elements within the structured light images, wherein the locations of the transition edges of the binary edge detection images are employed to identify corresponding non-transition edges within the respective structured light images;

employing the edge locations within the structured light images to decode the structured light pattern within the structured light images;

performing stereo matching of the decoded structured light images and obtaining a disparity map; and generating a reconstruction of the 3D surface based on the disparity map.

30. The system according to claim 29 wherein said projector is controlled by said computer hardware such that the structured light pattern is a binary structured light pattern.

31. The system according to claim 29 wherein said projector is controlled by said computer hardware such that the binary edge detection images comprise a binary comb pattern aligned with at least two adjacent elements of the structured light pattern that have a common state.

32. The system according to claim 29 wherein said projector is controlled by said computer hardware such that the binary edge detection pattern is a binary comb pattern.

33. The system according to claim 29 wherein said projector is controlled by said computer hardware such that the binary edge detection pattern includes transition edges that respectively correspond to each non-transition edge of the structured light pattern.

34. The system according to claim 29 wherein said projector is controlled by said computer hardware such that the binary edge detection pattern includes transition edges that respectively correspond to a subset of the non-transition edges of the structured light pattern.

35. The system according to claim 29 wherein said projector is controlled by said computer hardware such that the binary edge detection pattern is a first binary edge detection pattern and the binary edge detection images are first binary edge detection images, and wherein said computer hardware is further configured to perform operations comprising:

employing the projector to project an additional binary edge detection pattern onto the 3D surface and acquiring, with the first camera and the second camera, respective additional binary edge detection images of the projected additional binary edge detection pattern;

wherein the additional binary edge detection pattern is projected such that the elements of the projected additional binary edge detection pattern are spatially aligned with the elements of the projected structured light pattern, and such that a plurality of transition edges of the additional binary edge detection pattern are respectively aligned with non-transition edges of the projected structured light pattern; and wherein locations of transition edges determined in the additional binary edge detection images are employed to identify corresponding non-transition edges within the respective structured light images.

36. The system according to claim 35 wherein said projector is controlled by said computer hardware such that the additional binary edge detection pattern is an inverse of the first binary edge detection pattern.

37. The system according to claim 36 wherein said projector is controlled by said computer hardware such that the first binary edge detection pattern comprises a binary comb pattern.

38. The system according to claim 36 wherein said projector is controlled by said computer hardware such that the first binary edge detection pattern is a binary comb pattern.

39. The system according to claim 29 wherein said projector is controlled by said computer hardware such that the structured light pattern is a de Bruijn pattern.

40. The system according to claim 39 wherein said projector is controlled by said computer hardware such that the de Bruijn pattern is a binary de Bruijn pattern.

41. The system according to claim 39 wherein said projector is controlled by said computer hardware such that the de Bruijn pattern has an alphabet greater than two.

42. The system according to claim 40 wherein said projector is controlled by said computer hardware such that the projected binary de Bruijn pattern comprises two de Bruijn patterns that are projected in a common row, and wherein said computer hardware is further configured to perform operations comprising:

employing the projector to project at least one Gray code the 3D surface such that the Gray code pattern is spatially aligned with the common row;

acquiring, with the first camera and the second camera, respective Gray code images of the projected Gray code pattern;

employing the Gray code images to subdivide the projected binary de Bruijn pattern into regions respectively corresponding to the two de Bruijn patterns.

43. A system for obtaining structured light reconstruction of a 3D surface, the system comprising:

a projector configured to project patterns onto a surface;

a camera oriented to image the patterns projected by the projector; and computer hardware operatively coupled to said projector and said camera, wherein said computer hardware comprises memory coupled with one or more processors to store instructions, which when executed by the one or more processors, causes the one or more processors to perform operations comprising:

employing the projector to project a structured light pattern onto the 3D surface;

acquiring a structured light image of the projected structured light pattern with the camera;

employing the projector to project a binary edge detection pattern onto the 3D surface, wherein the binary edge detection pattern is projected such that the elements of the projected binary edge detection pattern are spatially aligned with the elements of the projected structured light pattern, and such that a plurality of transition edges of the binary edge detection pattern are respectively aligned with non-transition edges of the projected structured light pattern, wherein the transition edges correspond to boundaries between adjacent elements having different states, and the non-transition edges correspond to boundaries between adjacent elements having a common state;

acquiring a binary edge detection image of the projected binary edge detection pattern with the camera;

processing the binary edge detection image to identify locations of the transition edges;

determining edge locations of elements within the structured light image, wherein the locations of the transition edges of the binary edge detection image are employed to identify corresponding non-transition edges within the structured light image;

employing the edge locations within the structured light image to decode the structured light pattern within the structured light image;

performing stereo matching of the decoded structured light image with a reference and obtaining a disparity map; and generating a reconstruction of the 3D surface based on the disparity map.

44. The system according to claim 43 wherein said projector is controlled by said computer hardware such that wherein the structured light pattern is a binary structured light pattern.

45. The system according to claim 43 wherein said projector is controlled by said computer hardware such that the binary edge detection images comprise a binary comb pattern aligned with at least two adjacent elements of the structured light pattern that have a common state.

46. The system according to claim 43 wherein said projector is controlled by said computer hardware such that the binary edge detection pattern is a binary comb pattern.

47. The system according to claim 43 wherein said projector is controlled by said computer hardware such that the binary edge detection pattern includes transition edges that respectively correspond to each non-transition edge of the structured light pattern.

48. The system according to claim 43 wherein said projector is controlled by said computer hardware such that the binary edge detection pattern includes transition edges that respectively correspond to a subset of the non-transition edges of the structured light pattern.

49. The system according to claim 43 wherein said projector is controlled by said computer hardware such that the binary edge detection pattern is a first binary edge detection pattern and the binary edge detection image is a first binary edge detection image, wherein said computer hardware is further configured to perform operations comprising:
  employing the projector to project an additional binary edge detection pattern onto the 3D surface and acquiring, with the camera, an additional binary edge detection image of the projected additional binary edge detection pattern;
  wherein the additional binary edge detection pattern is projected such that the elements of the projected additional binary edge detection pattern are spatially aligned with the elements of the projected structured light pattern, and such that a plurality of transition edges of the additional binary edge detection pattern are respectively aligned with non-transition edges of the projected structured light pattern; and
  wherein locations of transition edges determined in the additional binary edge detection image are employed to identify corresponding non-transition edges within the structured light image.

50. The system according to claim 49 wherein said projector is controlled by said computer hardware such that the additional binary edge detection pattern is an inverse of the first binary edge detection pattern.

51. The system according to claim 50 wherein said projector is controlled by said computer hardware such that the first binary edge detection pattern comprises a binary comb pattern.

52. The system according to claim 50 wherein said projector is controlled by said computer hardware such that the first binary edge detection pattern is a binary comb pattern.

53. The system according to claim 43 wherein said projector is controlled by said computer hardware such that the structured light pattern is a de Bruijn pattern.

54. The system according to claim 53 wherein said projector is controlled by said computer hardware such that the de Bruijn pattern is a binary de Bruijn pattern.

55. The system according to claim 53 wherein said projector is controlled by said computer hardware such that the de Bruijn pattern has an alphabet greater than two.

56. The system according to claim 54 wherein said projector is controlled by said computer hardware such that the projected binary de Bruijn pattern comprises two de Bruijn patterns that are projected in a common row, and wherein said computer hardware is further configured to perform operations comprising:
  employing the projector to project at least one Gray code the 3D surface such that the Gray code pattern is spatially aligned with the common row;
  acquiring, with the camera, respective Gray code images of the projected Gray code pattern;
  employing the Gray code image to subdivide the projected binary de Bruijn pattern into regions respectively corresponding to the two de Bruijn patterns.

* * * * *